United States Patent
Wang et al.

(10) Patent No.: US 9,938,207 B2
(45) Date of Patent: Apr. 10, 2018

(54) UPGRADING PARAFFINS TO DISTILLATES AND LUBE BASESTOCKS

(71) Applicants: Kun Wang, Bridgewater, NJ (US);
Robert T. Carr, High Bridge, NJ (US);
Elise Marucchi-Soos, Warren, NJ (US)

(72) Inventors: Kun Wang, Bridgewater, NJ (US);
Robert T. Carr, High Bridge, NJ (US);
Elise Marucchi-Soos, Warren, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 43 days.

(21) Appl. No.: 15/014,300

(22) Filed: Feb. 3, 2016

(65) Prior Publication Data
US 2016/0237004 A1    Aug. 18, 2016

Related U.S. Application Data

(60) Provisional application No. 62/117,540, filed on Feb. 18, 2015.

(51) Int. Cl.
| | |
|---|---|
| C07C 2/12 | (2006.01) |
| C07C 5/333 | (2006.01) |
| C07C 5/03 | (2006.01) |
| C07C 2/58 | (2006.01) |
| C10G 50/00 | (2006.01) |
| B01J 29/12 | (2006.01) |
| B01J 29/22 | (2006.01) |
| B01J 29/44 | (2006.01) |
| B01J 29/74 | (2006.01) |

(52) U.S. Cl.
CPC .............. *C07C 5/3337* (2013.01); *B01J 29/12* (2013.01); *B01J 29/22* (2013.01); *B01J 29/44* (2013.01); *B01J 29/7415* (2013.01); *B01J 29/7461* (2013.01); *B01J 29/7492* (2013.01); *C07C 2/12* (2013.01); *C07C 2/58* (2013.01); *C10G 50/00* (2013.01); *B01J 2229/186* (2013.01); *C07C 2529/74* (2013.01); *C10G 2300/1081* (2013.01)

(58) Field of Classification Search
CPC .............. C07C 2/12; C07C 5/333; C07C 5/03
USPC .......................... 585/312, 700, 654, 660, 533
See application file for complete search history.

(56) References Cited

U.S. PATENT DOCUMENTS

| | | |
|---|---|---|
| 3,668,268 A | 6/1972 | Mulaskey |
| 4,686,316 A | 8/1987 | Morrison |
| 5,864,052 A | 1/1999 | Nierlich et al. |

(Continued)

FOREIGN PATENT DOCUMENTS

WO    2014073006 A1    5/2014

OTHER PUBLICATIONS

PCT/US2016/016291 International Search Report and Written Opinion dated Apr. 19, 2016.

(Continued)

*Primary Examiner* — Thuan D Dang
(74) *Attorney, Agent, or Firm* — Andrew T. Ward

(57) ABSTRACT

A process for converting paraffins, especially light paraffins, e.g. $C_3$-$C_8$ paraffins, to higher boiling range paraffinic liquid hydrocarbons comprises endothermically dehydrogenating the light paraffin combined with a thermally coupled, exothermic reaction such as olefin oligomerization to supply heat for the endothermic conversion.

12 Claims, 4 Drawing Sheets

(56) References Cited

U.S. PATENT DOCUMENTS

Figure 1:
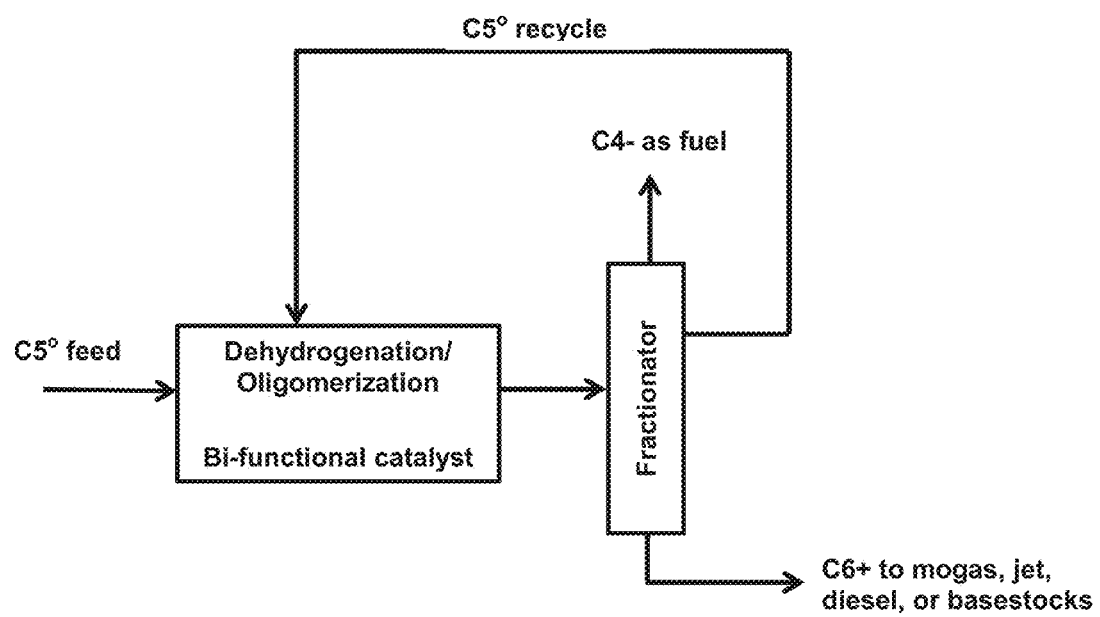

| | | |
|---|---|---|
| 5,994,601 A | 11/1999 | Nierlich et al. |
| 5,998,685 A | 12/1999 | Nierlich et al. |
| 2002/0026087 A1 | 2/2002 | Nierlich et al. |
| 2013/0090503 A1* | 4/2013 | Goldman .................. C07C 2/74 585/255 |

OTHER PUBLICATIONS

Bhasin et al., "Dehydrogenation and oxydehydrogenation of paraffins to olefins", Applied Catalysts A: General, Nov. 2001, pp. 397-419, vol. 221, No. 1-2, Elsevier.
"Catofin Dehydrogenation", Chicago Bridge & Iron Company, Lummus-Technology.
"Technology Profile: STAR process", Uhde Gmbh, Online article, Feb. 17, 2015.
"Process Technology and Equipment: Oleflex Process for Propylene Production", Petrochemical, 2004 UOP, LLC.

* cited by examiner

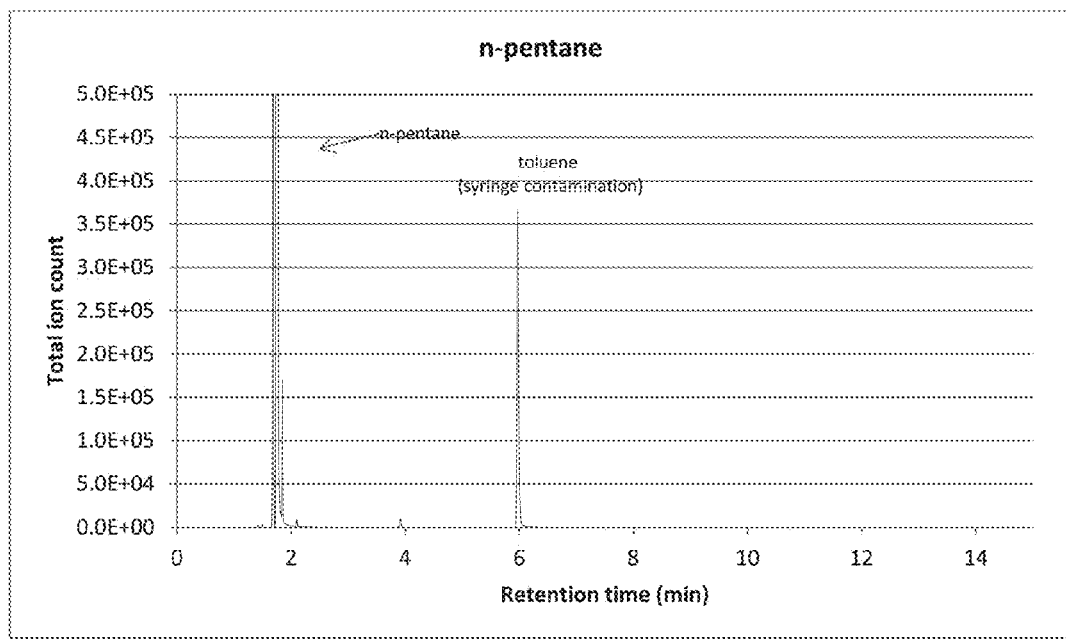
Figure 2a: GC-MS trace for the n-pentane feed in Example 1.
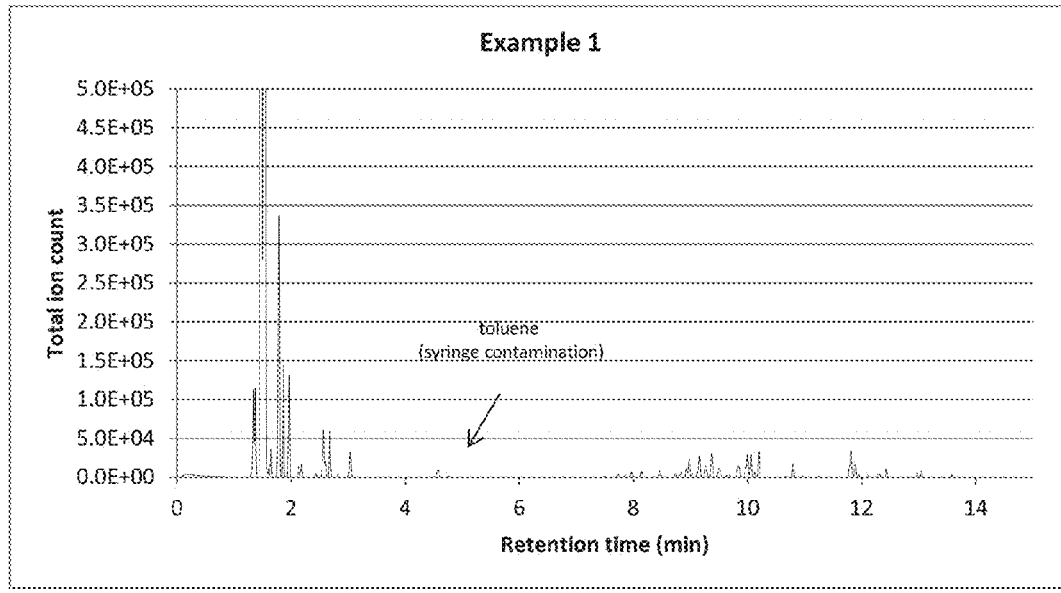
Figure 2b: GC-MS trace of products from Example 1.

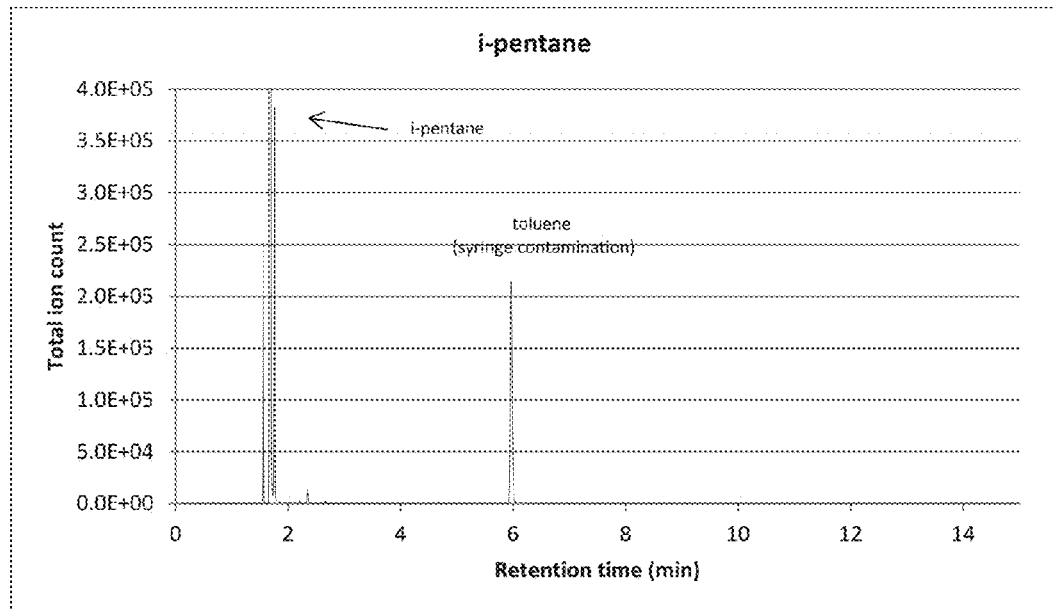
Figure 3a: GC-MS trace for the i-pentane feed in Example 2.
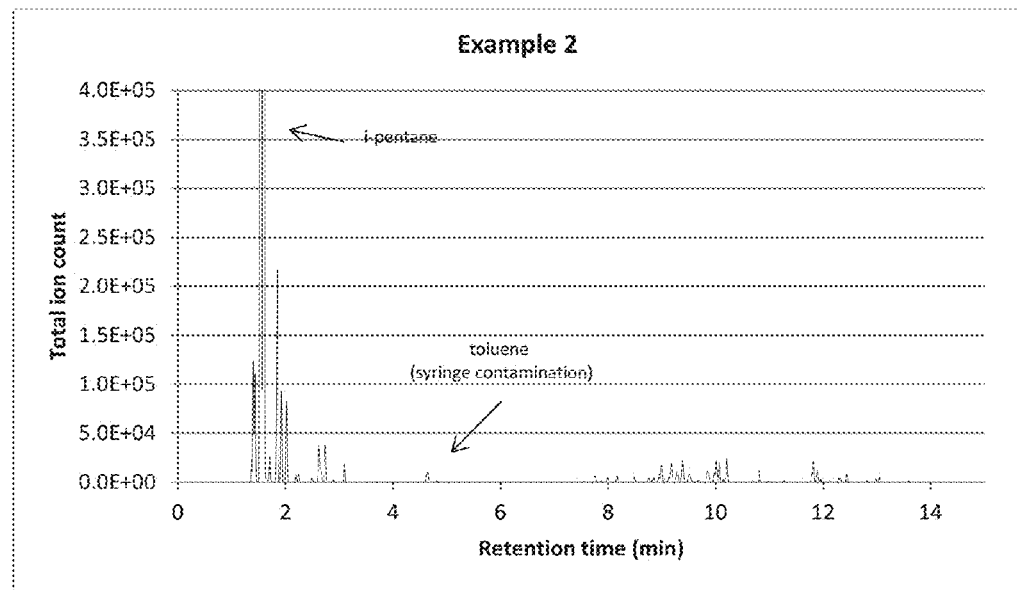
Figure 3b: GC-MS trace of products from Example 2.

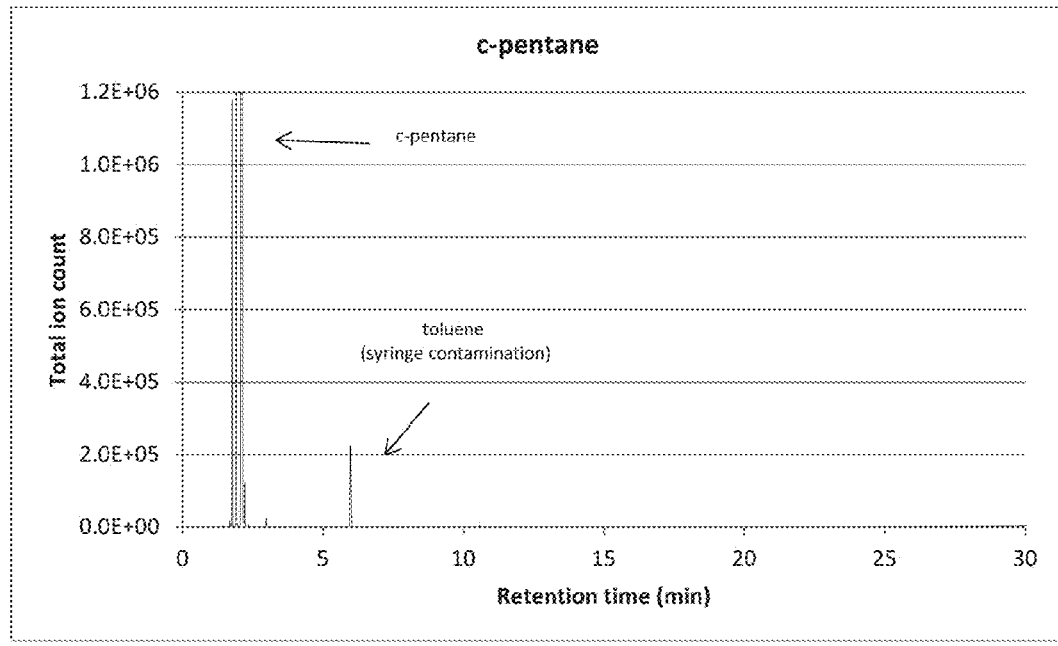
Figure 4a: GC-MS trace for the c-pentane feed in Example 3.
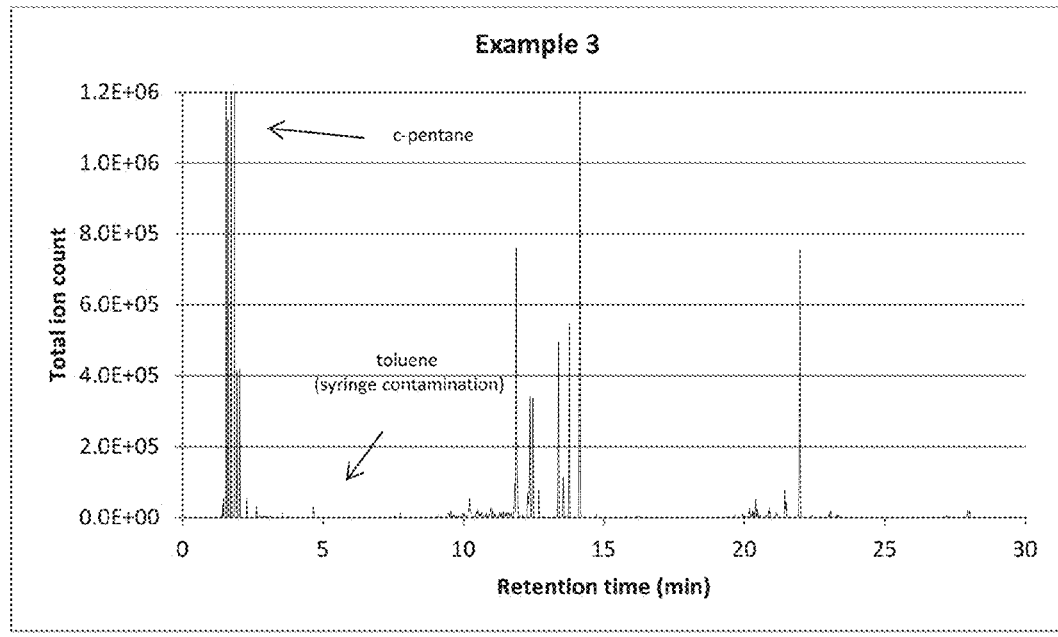
Figure 4b: GC-MS trace of products from Example 3.

UPGRADING PARAFFINS TO DISTILLATES AND LUBE BASESTOCKS

CROSS-REFERENCE TO RELATED APPLICATIONS

This application claims priority to U.S. Provisional Application Ser. No. 62/117,540 filed on Feb. 18, 2015.

FIELD OF THE INVENTION

This invention relates to a process to upgrade paraffins to higher value products such as lubricant basestocks, jet and diesel fuels. The process is particularly applicable to the upgrading of light paraffins ($C_3$-$C_8$) which are presently in abundant supply in the United States. Light paraffins of this kind are commonly found in Natural Gas Liquids (NGL), tight oils (light crude oil contained in petroleum-bearing formations of low permeability, often shale or tight sandstone, also referred to as light tight oils), as well as fractions from various refining and/or chemical streams.

BACKGROUND OF THE INVENTION

With the increasing production of shale gas and tight oils, the supply of light paraffins (e.g., $C_2$-$C_8$, especially $C_2$-$C_5$ paraffins) is increasing at an unprecedented rate in the North America region; a large fraction (up to 30%) of NGL, for example, is $C_4$/$C_5$ paraffins. At the same time, demand for $C_4$/$C_5$ molecules is decreasing due to a number of factors: 1) steam crackers switching feed from light naphtha to ethane; 2) shrinkage of gasoline pool in the North American market; and 3) a potential mandate for gasoline Reid Vapor Pressure (RVP) reduction. Although diluent use of $C_5$s for heavy crude is predicted to grow somewhat, the supply of $C_4$s/$C_5$s is quickly outpacing demand and the imbalance is becoming worse with time. Profitable dispositions for ethane (e.g., cracking to make ethylene) and propane (e.g., dehydrogenation making propylene) exist. Upgrading $C_4$/$C_5$ paraffins to higher value and large volume products while desirable, remains challenging. Conversion of $C_4$/$C_5$ paraffins to heavier hydrocarbon products such as kerojet, diesel fuels as well as lube basestocks would provide a large volume and higher value outlet to help alleviate the excess of light ends in the North American market but there is no current commercial process directly converting light paraffins to heavier hydrocarbons such as these. Conventional upgrading practices typically first convert light paraffins to olefins via cracking or dehydrogenation, followed by olefin chemistries such as oligomerization or polymerization, alkylation, etc. to build higher molecular weight molecules.

A number of technologies are known to convert light paraffins to aromatics such as BTX (benzene, toluene, and xylenes). Examples of such technologies include the Cyclar™ process developed by UOP and the M2-Foming developed by Mobil Oil Corporation.

Dehydrogenation of light paraffins such as propane and iso-butane is commercially practiced; and the processes are designed to isolate high purity olefins as the final product. Current state-of-the-art processes use either Pt-based catalyst (e.g., UOP Oleflex™) or Cr-based catalyst (Houdry Catofin™ licensed by CB&I). Due to thermodynamic limitations, high temperature (>500° C.) and low pressure (vacuum or dilution with steam) are needed in order to favor the dehydrogenation reaction. Consequently, the catalyst deactivates quickly and frequent regeneration (oxychlorination for Pt-based catalysts; air burn for Cr-based catalysts) is necessary.

A number of patent publications from Nierlich et al. describe processes for converting butane to unsaturated products which could then be further reacted to produce industrially useful materials. U.S. Pat. No. 5,864,052 describes a process for preparing di-n-butene and alkyl tert-butyl ethers from field butanes by dehydrogenation and oligomerization. U.S. Pat. No. 5,994,601 describes a process for preparing butene oligomers from Fischer-Tropsh olefins by oligomerization to form dibutene. U.S. Pat. No. 5,998,685 describes the synthesis of butene oligomers by dehydrogenation of field butanes and oligomerization over a nickel-containing material such as alumina or montmorillonite. US 2002/0026087 utilizes a similar dehydrogenation/oligomerization route, again using a nickel based catalyst.

Bhasin et al, *Dehydrogenation and oxydehydrogenation of paraffins to olefins*, Applied Catalysts A: General 221 (2001) 397-419, provide an overview of processes for the production of olefins from paraffins by dehydrogenation and oxidative dehydrogenation.

The principle of balancing heat requirement for successive reactions is utilized in the Uhde STAR Process® for light olefin production which converts a $C_3$/$C_4$ paraffin feed (with recycle) in a strongly endothermic dehydrogenation reaction at 500-600° C. and 6-9 bar over a noble metal/zinc catalyst impregnated on calcium aluminate support. Part of the hydrogen from the intermediate reaction product leaving the reformer is reacted selectively with oxygen or oxygen-enriched air in an adiabatic catalytic oxy-reactor to form steam, followed by further dehydrogenation of unconverted paraffin over the same catalyst. Internally supplied heat from the exothermic hydrogen conversion reduces the external heat required for the endothermic dehydrogenation.

SUMMARY OF THE INVENTION

We have now developed a process for converting paraffins to higher boiling range liquid hydrocarbons. The process is especially applicable to light paraffins, e.g. $C_3$-$C_8$ paraffins, particularly light paraffins ($C_4$/$C_5$) which are currently in good supply. By the use of a bi-functional catalyst (with acid activity and hydrogenation/dehydrogenation activity) in a single step, heavier hydrocarbon products, predominantly paraffins, are formed. The process effectively couples paraffin dehydrogenation with exothermic olefin reactions including oligomerization and re-hydrogenation in a single step. A number of benefits are conferred in this process: 1) it couples an endothermic reaction with exothermic reactions, making the overall reaction thermodynamics more favorable than dehydrogenation alone; 2) it saturates the olefin oligomers with hydrogenation giving primarily paraffinic products, which are desirable as fuels and lubricant basestocks.

Without being bound to any theory or reaction mechanism, the process for converting paraffins, especially light paraffins, e.g. $C_3$-$C_8$ paraffins, to higher boiling range paraffinic liquid hydrocarbons comprises dehydrogenating a light paraffin to form an olefinic product and reacting the olefin in exothermic reactions to supply heat for the endothermic dehydrogenation reaction. The preferred exothermic reactions for the olefin intermediates comprise oligomerization to form higher boiling point olefins and subsequent hydrogenation to paraffinic hydrocarbons. The endothermic dehydrogenation reaction and exothermic reactions described above may be carried out in the presence of a single, bi-functional catalyst having acidic and hydrogenation/dehydrogenation activity. Other exothermic olefin addition reactions using co-reactants may also be used; for example, hydroformylation, hydration, etherification, carboxylation or alkylation to supply the heat requirements of the initial dehydrogenation.

DRAWINGS

In the accompanying drawings:
FIG. 1 is a process schematic for converting pentane to heavier hydrocarbons.
FIGS. 2a, 2b, 3a, 3b, 4a and 4b show the GC-MS traces for the feeds and reaction products respectively of Examples 1, 2 and 3.

DETAILED DESCRIPTION

While the paraffin dehydrogenation reaction is strongly endothermic, most chemical transformations of a carbon-carbon double bond are exothermic due to the fact that the C—C pi-bond is relatively weak (ca. 63 kcal/mole) relative to the sigma-bonds formed to the atoms or groups of the reactant. Consequently, if the bond energies of the product molecules are greater than the bond energies of the reactants, the reaction will be exothermic. Thus, the combination of an olefin addition reaction with the endothermic paraffin dehydrogenation reaction offers an opportunity for the effective conversion of light paraffins to higher boiling and more valuable hydrocarbons.

Exemplary chemistries applicable to this process scheme are shown below using pentane as feed and olefin oligomerization/hydrogenation as the cascade reactions:

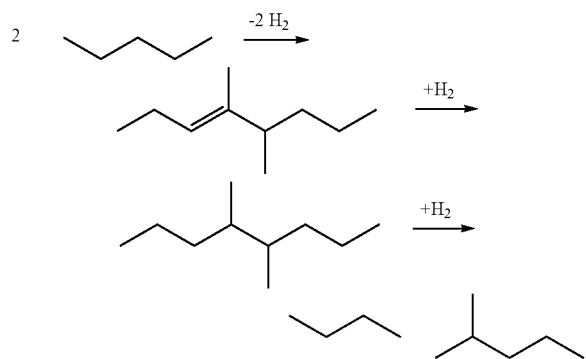

The thermodynamics for pentane dehydrogenation followed by a cascade oligomerization reaction forming isodecane is unfavorable as shown by the first equation.

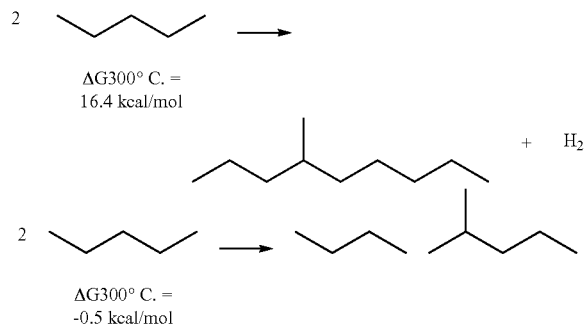

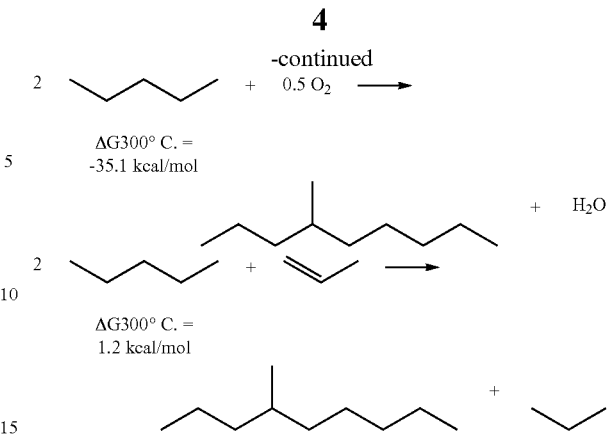

When coupled with exothermic reactions such as olefin oligomerization, chemically consuming the $H_2$ via combustion (forming water), saturation of olefins (the olefins to be saturated can be the olefinic oligomers or a second olefin such as ethylene or propylene that is co-fed to the reaction), or hydrogenolysis and/or cracking of paraffins (give both higher and lower carbon number paraffins), the overall reaction thermodynamics is significantly improved. By coupling the endothermic reactions with exothermic reactions, the free energy of reaction is improved significantly and the overall reaction may become thermodynamically favorable if the relative extents of the endothermic and exothermic reactions are controlled by appropriate adjustment of reactant ratios. Other potentially applicable exothermic olefin addition reactions include hydroformylation, carboxylation, hydration, etherification and alkylation.

FIG. 1 illustrates a process flow scheme for effecting the conversion of pentane in a single reactor using bi-functional catalysts, in which the heat from exothermic reactions is used to balance the heat requirement of the endothermic dehydrogenation reaction. Although pentane is used as an illustration in this instant application, the feed can be any paraffin, either alone or in combination with other paraffins, in the $C_3$ to $C_8$ carbon number range. The feed can comprise linear, branched, or cyclic paraffins in the $C_3$-$C_8$ carbon number range. For example, the feed can comprise natural gas liquid, natural gas condensate, natural gasoline, or light virgin naphtha.

In FIG. 1, the pentane feed is subjected to a bi-functional catalyst, and is effectively converted to heavier hydrocarbons together with fractions of lighter hydrocarbons. The bi-functional catalyst comprises a metal component with dehydrogenation/hydrogenation function and an acidic component that can affect exothermic olefin reactions such as oligomerization. The initial dehydrogenated products comprising pentenes, unreacted pentane and hydrogen are converted by the acidic function of the catalyst forming higher molecular weight olefins (e.g., via oligomerization), which are further converted to saturated hydrocarbons, consuming the hydrogen, via the hydrogenation functions on the catalyst. In this reaction, the pentene is converted to decane, decene and other $C_5$+ hydrocarbons with a significant yield of saturated paraffins resulting from hydrogenation of the intermediate olefin oligomers by the hydrogen generated in the reactor. Products may typically comprise hydrocarbons in the gasoline boiling range including saturates such as decane with some residual olefins such as decene as well as higher boiling, middle distillate hydrocarbons such as products in the kerojet and road diesel boiling range, e.g. JP-5, JP-8, 1-D, 2-D diesel (ASTM D-975) or even higher boiling products such as lube basestocks. The reaction products from the reactor then pass to the fractionation column where the lighter components such as $C_4$- hydrocarbons and $H_2$ are removed and used as process fuel. Unreacted pentane is recycled to the reactor. In the absence of heteroatom contaminants in the feed, the products will contain no sulfur or nitrogen, rendering them suitable for use as clean fuels.

The paraffin dehydrogenation and exothermic olefin reactions may be carried out in cascade in a single reactor, as illustrated in the Examples, using a single slurry phase reactor. Alternatively, the sequential reactions may be carried out in separate reaction zones which are thermally coupled in order to transfer the heat generated in the exothermic oligomerization reaction to the dehydrogenation zone, for example, by using reaction zones coupled by means of heat pipes or by using other thermal couplings e.g. in a shell and tube type reactor with one reaction taking place on the tube side and the other on the shell side. In this way the reaction conditions in each reactor can be controlled and optimized independently without losing the benefit of the heat balancing process. The use of separate reaction zones is suited to cases where the exotherm from an olefin conversion reaction is exploited to balance the heat requirement of the dehydrogenation.

The dehydrogenation/hydrogenation and acid functions are typically appropriate for both the dehydrogenation and subsequent exothermic reactions; the two functions can be on the same catalyst or on separate catalysts. The dehydrogenation/hydrogenation function comprises a noble or non-noble metal such as Pt, Pd, Ni, Co, Fe, Sn, Rh, Ir, Ru, Re, W, Mo, or In, either as a single component or binary or ternary component in the form of alloys or solid solutions. The dehydrogenation/hydrogenation function can be a Pt-based catalyst (e.g., Pt or Pt—Sn on alumina or other support) or a non-noble metal such as nickel, molybdenum, cobalt, e.g. in Group VI/VIII combinations such as Ni/W, Ni/Mo, Co/Mo. The preferred dehydrogenation/hydrogenation component is a Pt-based catalyst, e.g. Pt, Pt—Sn, Pt—Re, Pt—In on a support such as alumina, silica, zirconia, titania, ceria, lanthanum oxide, magnesium oxide, either alone or mixtures thereof. The preferred olefin oligomerization function is an acidic solid such as zeolite, silicoaluminophosphate (SAPO), aluminosilicate, acidic clay, or acidic metal oxides such as sulfated zirconia, $WO_x/ZrO_2$, or $MoO_x/ZrO_2$. Bi-functional catalysts containing the dehydrogenation/hydrogenation and acid functions on the same catalyst are preferred, including metallated molecular sieves, especially metal-functionalized zeolites such as Pt supported on a zeolite such as Pt/ZSM-48, Pt/ZSM-23, Pt/zeolite beta with the noble metals such as platinum or palladium being preferred.

When operating in a single reactor, the process is preferably carried out in a slurry phase, where the heavy products from the oligomerization are dissolved by the paraffins, keeping them from depositing on the catalyst surface causing deactivation. The reaction is typically carried out at a temperature in the range of 150-500° C. (preferably 200-350° C.), at a pressure of 2000 to 14000 kPag (about 300 to 2000 psig), preferably 3,500 kPag to 10,000 kPag (about 500-1500 psig), and a residence time of 1-24 h, preferably 2-10 h. The dehydrogenation can be improved by selectively removing hydrogen in order to shift the equilibrium towards the olefin product although restoration of a portion of the hydrogen will be required for the production of paraffins following the oligomerization step. Methods to remove the evolved hydrogen include: using an $H_2$-selective membrane reactor, reactive removal using a hydrogen acceptor such as oxygen or an unsaturated compound such as an olefin, or alkyne (e.g., acetylene) as noted above. Removal of hydrogen is particularly suitable for reactions where the addition reaction requires a co-reactant, e.g. as in hydroformylation, carboxylation, hydration, etherification, alkylation etc. for the manufacture of functionalized products.

The following non-limiting examples serve to demonstrate the process by converting pentanes with a bi-functional catalyst in a batch reactor.

EXAMPLE 1

Conversion of N-Pentane to Heavier Hydrocarbons

In a 5 mL Swagelok™ cell, 3.0 mL of n-pentane was mixed with 0.25 g of a Pt/ZSM-48 catalyst (0.6% Pt). The cell was sealed and placed in a sand bath and heated at 300° C. for 24 h. The cell was cooled to room temperature, and then chilled in an ice-bath before it was opened. The liquid product was recovered quickly and analyzed by GC-MS. The GC-MS trace for the feed is shown in FIG. 2a indicating that apart from toluene contamination introduced by the syringe into the GC, the feed was pure n-pentane; the product distribution is shown in Table 1 and in FIG. 2b indicating formation of higher molecular weight paraffins and some formation of lighter paraffins.

TABLE 1

Product distribution by GC-MS for Example 1

| Species | % (by Mass Spectrometry) |
|---|---|
| $C_4$ paraffins | 3.07 |
| $C_5$ paraffins | 73.82 |
| $C_6$ paraffins | 10.43 |
| $C_7$ paraffins | 3.56 |
| $C_{10}$ paraffins | 6.71 |
| $C_{10}$ aromatics | 2.1 |

EXAMPLE 2

Conversion of I-Pentane to Heavier Hydrocarbons

In a 5 mL Swagelok Cell™, 3.0 mL of i-pentane was mixed with 0.25 g of Pt/ZSM-48 catalyst (0.6% Pt). The cell was sealed and placed in a sand bath and heated at 300° C. for 24 h. The cell was cooled down to room temperature, then chilled in an ice-bath before it was opened. The liquid product was recovered quickly and analyzed by GC-MS. The GC-MS trace for the feed is shown in FIG. 3a indicating that apart from toluene contamination introduced by the syringe into the GC, the feed was pure n-pentane; the product distribution is shown in Table 2 and in FIG. 3b indicating formation of higher molecular weight paraffins and some lighter paraffins.

TABLE 2

Product distribution by GC-MS for Example 2

| Species | % (by Mass Spectrometry) |
|---|---|
| $C_3$ paraffin | 0.32 |
| $C_4$ paraffins | 3.61 |
| $C_5$ paraffins | 78.34 |

TABLE 2-continued

Product distribution by GC-MS for Example 2

| Species | % (by Mass Spectrometry) |
|---|---|
| $C_6$ paraffins | 7.75 |
| $C_7$ paraffins | 2.32 |
| $C_{10}$ paraffins | 5.36 |
| $C_{10}$ aromatics | 1.54 |

EXAMPLE 3

Conversion of C-Pentane to Heavier Hydrocarbons

In a 5 mL Swagelok™ cell, 3.0 mL of c-pentane (cyclopentane) was mixed with 0.25 g of Pt/ZSM-48 catalyst (0.6% Pt). The cell was sealed and placed in a sand bath and heated at 300° C. for 24 h. The cell was cooled down to room temperature, then chilled in an ice-bath before it was opened. The liquid product was recovered quickly and analyzed by GC-MS. The GC-MS trace is shown in FIG. 4a indicating that apart from toluene contamination introduced by the syringe into the GC, the feed was pure n-pentane; and the product distribution is shown in Table 3 and in FIG. 4b indicating formation of higher molecular weight species and lighter species.

TABLE 3

Product distribution by GC-MS for Example 3

| Species | % (by Mass Spectrometry) |
|---|---|
| $C_4$ | 0.41 |
| $C_5$ | 42.52 |
| $C_6$ | 4.66 |
| $C_{10}$ | 41.08 |
| $C_{15}$ | 9.88 |
| $C_{20}$ | 0.43 |

What is claimed is:

1. A process for converting light paraffins to higher boiling range paraffinic liquid hydrocarbons, comprising catalytically dehydrogenating a light paraffin in an endothermic reaction to form an olefinic reaction product; and
supplying heat to the endothermic dehydrogenation reaction from at least one exothermic reaction, the exothermic reaction being oligomerization of the olefin reaction product, in the same reactor to convert the olefin reaction products to heavier paraffins;
wherein the process is carried out at a temperature in the range of 200-350° C.;
wherein the paraffin dehydrogenation and olefin oligomerization are carried out in the presence of a single bi-functional solid catalyst consisting essentially of a noble metal on an acidic component.

2. A process according to claim 1 in which the acidic component is a zeolite.

3. A process according to claim 1 in which the noble metal is Pt, Pd, Ru, Rh, or Ir.

4. A process according to claim 1 in which the bi-functional solid catalyst consisting essentially of platinum on zeolite ZSM-5, ZSM-23, ZSM-48, Faujasite, Mordenite, or zeolite Beta.

5. A process according to claim 1 in which the paraffin comprises $C_3$-$C_8$ paraffins.

6. A process according to claim 1 in which the paraffin comprises butanes.

7. A process according to claim 1 in which the paraffin comprises pentanes.

8. A process according to claim 1 in which the paraffin comprises light virgin naphtha.

9. A process according to claim 1 in which the paraffin comprises natural gas liquids.

10. A process according to claim 1 in which the paraffin dehydrogenation and exothermic reactions are carried out in a thermally-coupled reactor; wherein the thermally-coupled reactor comprises one of (1) a reactor with an oligomerization zone and a dehydrogentation zone that are coupled via heat pipes, and (2) a shell and tube reactor wherein the exothermic oligomerization reaction takes place on the shell or tube side of the reactor and the endothermic dehydrogenation reaction takes place on the side of the reactor that the exothermic oligomerization reaction does not take place.

11. A process according to claim 1 in which the equilibrium of the paraffin dehydrogenation is shifted towards dehydrogenation by removal of hydrogen.

12. A process according to claim 1 in which pentanes are converted to $C_{10}$ or higher hydrocarbons.

* * * * *